United States Patent
Endo et al.

(10) Patent No.: US 10,683,301 B2
(45) Date of Patent: Jun. 16, 2020

(54) NITROGEN-CONTAINING CYCLIC COMPOUNDS AND METHODS FOR PRODUCING THE SAME

(71) Applicant: NISSAN CHEMICAL CORPORATION, Tokyo (JP)

(72) Inventors: Masahisa Endo, Toyama (JP); Gun Son, Toyama (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 16/473,172

(22) PCT Filed: Dec. 8, 2017

(86) PCT No.: PCT/JP2017/044198
§ 371 (c)(1),
(2) Date: Jun. 24, 2019

(87) PCT Pub. No.: WO2018/116872
PCT Pub. Date: Jun. 28, 2018

(65) Prior Publication Data
US 2020/0087308 A1     Mar. 19, 2020

(30) Foreign Application Priority Data

Dec. 22, 2016 (JP) .................. 2016-248959

(51) Int. Cl.
*C07D 489/04*    (2006.01)
*C07D 487/04*    (2006.01)

(52) U.S. Cl.
CPC ................ *C07D 487/04* (2013.01)

(58) Field of Classification Search
CPC .................................. C07D 487/04
See application file for complete search history.

(56) References Cited

U.S. PATENT DOCUMENTS 5,180,835 A    1/1993    Jacobs, III et al.

FOREIGN PATENT DOCUMENTS

| JP | H05-262772 A | 10/1993 |
|---|---|---|
| JP | 3154819 B2 | 4/2001 |
| JP | 2013-33276 A | 2/2013 |
| JP | 2015-54856 A | 3/2015 |
| JP | 2015-194748 A | 11/2015 |
| JP | 2016-138051 A | 8/2016 |
| WO | 2015/163352 A1 | 10/2015 |

OTHER PUBLICATIONS

Mar. 13, 2018 Search Report issued in International Patent Application No. PCT/JP2017/044198.
Mar. 13, 2018 Translation of Written Opinion issued in International Patent Application No. PCT/JP2017/044198.

*Primary Examiner* — Shawquia Jackson
(74) *Attorney, Agent, or Firm* — Oliff PLC

(57) ABSTRACT

There are provided novel glycolurils, and methods for producing the same. A nitrogen-containing cyclic compound of following formula (1):

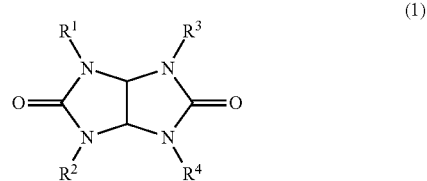

(1)

(wherein any two of $R^1$, $R^2$, $R^3$, and $R^4$ are glycidyl groups, and the remaining two are methoxymethyl groups), and the nitrogen-containing cyclic compound of formula (1) is represented by, for example, following formula (1A) or (1B):

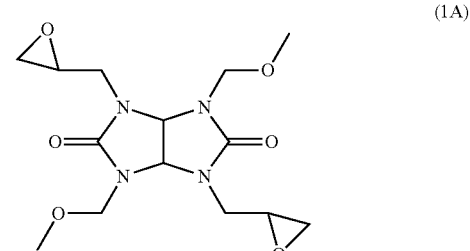

(1A)

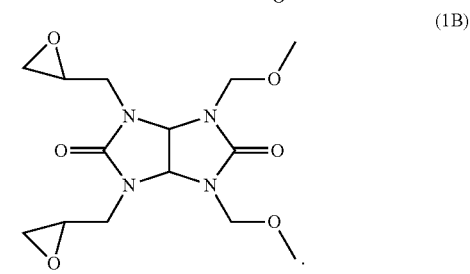

(1B)

4 Claims, No Drawings

NITROGEN-CONTAINING CYCLIC COMPOUNDS AND METHODS FOR PRODUCING THE SAME

TECHNICAL FIELD

The present invention relates to novel glycolurils each having two glycidyl groups and two methoxymethyl groups in one molecule, and methods for producing the same.

BACKGROUND ART

Glycolurils are heterocyclic compounds each having four urea nitrogen atoms in its ring structure. Glycolurils having various substituents on the urea nitrogen atoms have been produced and used as functional compounds.

For example, 1,3,4,6-tetrakis(methoxymethyl)glycoluril having four methoxymethyl groups in one molecule is well-known as a crosslinking agent for epoxy resins (see Patent Document 1).

Patent Document 2, for example, discloses a method for introducing four methoxymethyl groups into one molecule of a glycoluril having no substituent. Furthermore, Patent Document 3 discloses a glycidylglycoluril in which at least one of the hydrogen atoms attached to the four nitrogen atoms of a glycoluril is substituted with a glycidyl group. However, Patent Documents 1, 2, and 3 neither describe nor suggest a compound in which the hydrogen atoms attached to two of the four nitrogen atoms of a glycoluril are substituted with glycidyl groups, and the hydrogen atoms attached to the remaining two nitrogen atoms are substituted with methoxymethyl groups.

PRIOR ART DOCUMENTS

Patent Documents

Patent Document 1: Japanese Patent Application Publication No. 2013-33276 (JP 2013-33276 A)
Patent Document 2: Specification of Japanese Patent No. 3,154,819 (JP 3,154,819 B)
Patent Document 3: Japanese Patent Application Publication No. 2015-54856 (JP 2015-54856 A)

SUMMARY OF THE INVENTION

Problem to be Solved by the Invention

A chain polymer is polymerized using, as raw material monomers, a compound having two glycidyl groups in one molecule and a compound having two hydroxy or carboxy groups in one molecule. A polymer solution of the polymerized polymer dissolved in a suitable solvent is applied onto a substrate, and then baked at a predetermined temperature to form a film on the substrate. However, because the polymers are weakly crosslinked, the film cannot be sufficiently cured; therefore, the above-described crosslinking agent is added to the polymer solution. Meanwhile, a desired cured film can be obtained without using a crosslinking agent, by adopting a polymer in which a crosslinkable group such as methoxymethyl group has been introduced into the molecule.

The present invention has been made based on the foregoing background, and an object of the present invention is to provide novel glycolurils each having two glycidyl groups and two methoxymethyl groups in one molecule.

Means for Solving the Problem

The present invention is a nitrogen-containing cyclic compound of formula (1):

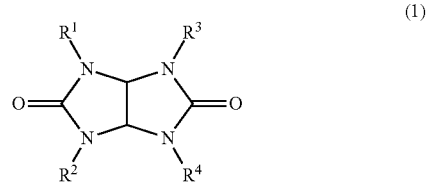

(1)

(wherein any two of $R^1$, $R^2$, $R^3$, and $R^4$ are glycidyl groups, and the remaining two are methoxymethyl groups).

The nitrogen-containing cyclic compound of formula (1) is represented by, for example, formula (1A) or (1B):

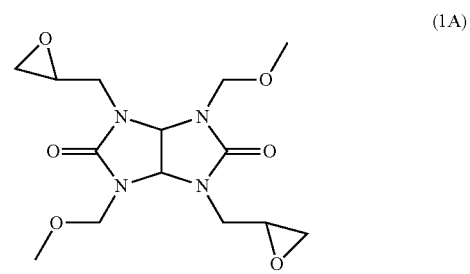

(1A)

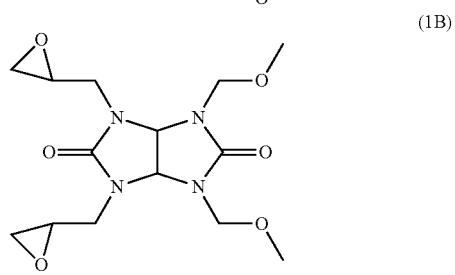

(1B)

Furthermore, the present invention is a method for producing a nitrogen-containing cyclic compound comprising:

a first step of obtaining a compound of formula (b) by reacting a compound of formula (a) with formaldehyde in a basic aqueous solution;

a second step of obtaining a compound of formula (c) by reacting the compound of formula (b) with methanol in an acid solution of the methanol; and a third step of obtaining the nitrogen-containing cyclic compound of formula (1A) by reacting the compound of formula (c) with an oxidizing agent in an organic solvent:

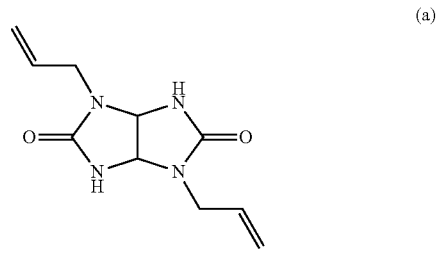

(a)

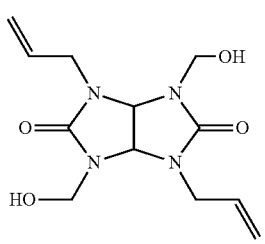
(b)

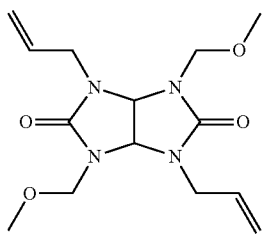
(c)

Furthermore, the present invention is a method for producing a nitrogen-containing cyclic compound comprising:

a first step of obtaining a compound of formula (e) by reacting a compound of formula (d) with formaldehyde in a basic aqueous solution;

a second step of obtaining a compound of formula (f) by reacting the compound of formula (e) with methanol in an acid solution of the methanol; and a third step of obtaining the nitrogen-containing cyclic compound of formula (1B) by reacting the compound of formula (f) with an oxidizing agent in an organic solvent:

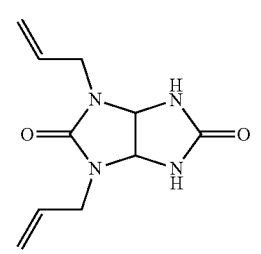
(d)

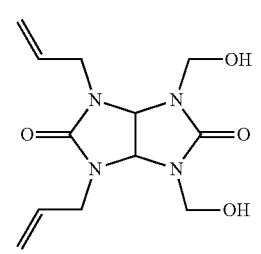
(e)

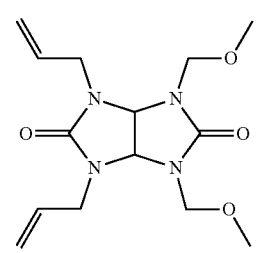
(f)

Effects of the Invention

The glycolurils according to the present invention are nitrogen-containing cyclic compounds each having two glycidyl groups and two methoxymethyl groups in one molecule, in which the glycidyl groups and the methoxymethyl groups are individually attached to different nitrogen atoms. These compounds have the two methoxymethyl groups, which are crosslinkable groups, and can therefore be used as crosslinking agents.

Each of the nitrogen-containing cyclic compounds of the present invention further has the two glycidyl groups, and therefore, a chain polymer can be polymerized using, as raw material monomers, the compound and a compound having two hydroxy or carboxy groups in one molecule. The polymerized polymer has the methoxymethyl groups derived from the nitrogen-containing cyclic compound, and therefore, a desired cured film having solvent resistance can be obtained without using a crosslinking agent other than the polymer.

MODES FOR CARRYING OUT THE INVENTION

The glycolurils of the present invention are nitrogen-containing cyclic compounds of formula (1). In formula (1), when $R^1$ and $R^4$ are each a glycidyl group, and $R^2$ and $R^3$ are each a methoxymethyl group, or when $R^2$ and $R^3$ are each a glycidyl group, and $R^1$ and $R^4$ are each a methoxymethyl group, the glycoluril of the present invention is a nitrogen-containing cyclic compound of formula (1A). Furthermore, in formula (1), when $R^1$ and $R^2$ are each a glycidyl group, and $R^3$ and $R^4$ are each a methoxymethyl group, or when $R^3$ and $R^4$ are each a glycidyl group, and $R^1$ and $R^2$ are each a methoxymethyl group, the glycoluril of the present invention is a nitrogen-containing cyclic compound of formula (1B).

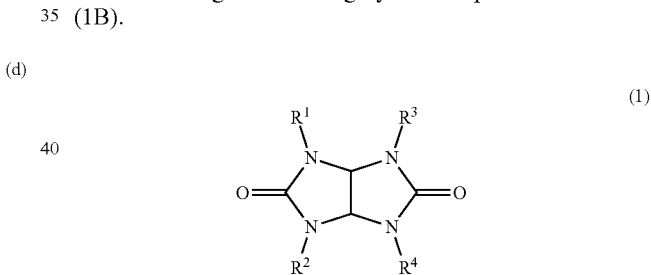
(1)

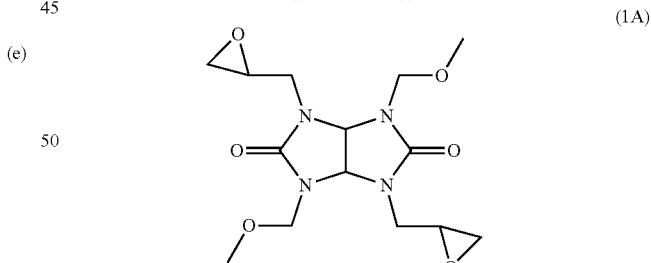
(1A)

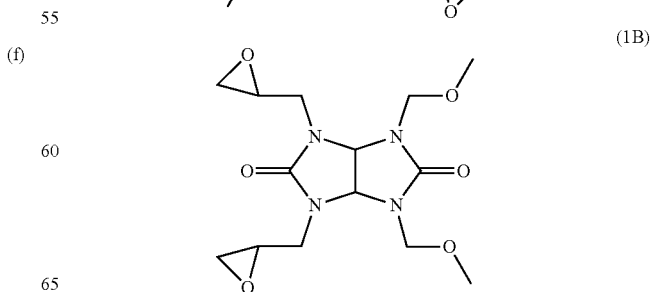
(1B)

(wherein any two of $R^1$, $R^2$, $R^3$, and $R^4$ are glycidyl groups, and the remaining two are methoxymethyl groups).

The nitrogen-containing cyclic compound of formula (1A) is produced through a first step of obtaining a compound of formula (b) by reacting a compound of formula (a) with formaldehyde in a basic aqueous solution; a second step of obtaining a compound of formula (c) by reacting the compound of formula (b) with methanol in an acid solution of the methanol; and a third step of reacting the compound of formula (c) with an oxidizing agent in an organic solvent.

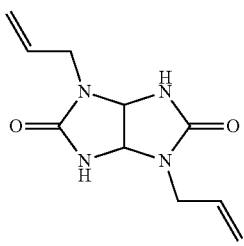
(a)

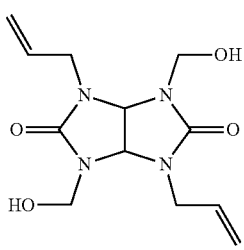
(b)

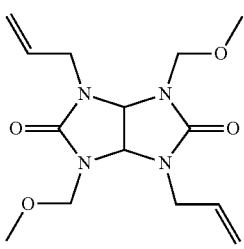
(c)

The nitrogen-containing cyclic compound of formula (1B) is produced through a first step of obtaining a compound of formula (e) by reacting a compound of formula (d) with formaldehyde in a basic aqueous solution; a second step of obtaining a compound of formula (f) by reacting the compound of formula (e) with methanol in an acid solution of the methanol; and a third step of reacting the compound of formula (f) with an oxidizing agent in an organic solvent.

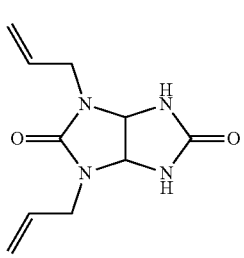
(d)

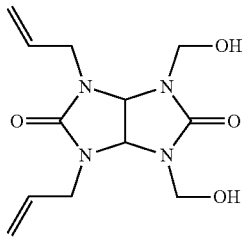
(e)

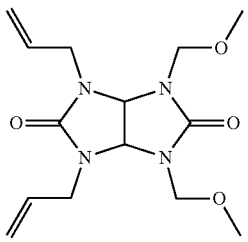
(f)

The compound of formula (a) can be synthesized based on, for example, Referential Example 3 (Synthesis of 1,4-diallylglycoluril) described in Japanese Patent Application Publication No. 2016-138051 (JP 2016-138051 A). As long as the compound of formula (a) is finally obtained, it may be synthesized using a method different from that described in Referential Example 3 above.

The compound of formula (d) can be synthesized based on, for example, Referential Example 1 (Synthesis of 1,3-diallylglycoluril) described in Patent Document 3 above or Referential Example 2 (Synthesis of 1,3-diallylglycoluril) described in Japanese Patent Application Publication No. 2016-138051 (JP 2016-138051 A). As long as the compound of formula (d) is finally obtained, it may be synthesized using a method different from those described in Referential Example 1 and Referential Example 2 above.

In the production processes of the nitrogen-containing cyclic compounds, examples of the basic aqueous solution include an aqueous solution of sodium hydroxide, an aqueous solution of potassium hydroxide, and an aqueous solution of sodium hydrogen carbonate. Examples of the acid in the acid solution of methanol include nitric acid, sulfuric acid, formic acid, and hydrochloric acid. Examples of the organic solvent include halogenated hydrocarbons, such as chloroform, dichloromethane, carbon tetrachloride, and 1,2-dichloroethane; alcohols, such as methanol, ethanol, and isopropyl alcohol; aliphatic hydrocarbons, such as hexane and heptane; amides, such as N,N-dimethylformamide, N,N-dimethylacetamide, N-methyl-2-pyrrolidone, and N-methylpyrrolidinone; and sulfoxides, such as dimethyl sulfoxide. Examples of the oxidizing agent include m-chloroperoxybenzoic acid, hydrogen peroxide, Oxone [registered trademark] (potassium peroxymonosulfate), and peracetic acid.

A polymer having a repeating unit structure of formula (2) is obtained by polymerizing the nitrogen-containing cyclic compound of formula (1A) with a compound having two carboxy or hydroxy groups in one molecule. A polymer having a repeating unit structure of formula (3) is obtained by polymerizing the nitrogen-containing cyclic compound of formula (1B), instead of the nitrogen-containing cyclic compound of formula (1A), with a compound having two carboxy or hydroxy groups in one molecule. Instead of the compound having two carboxy or hydroxy groups in one molecule, a compound having at least one carboxy group and at least one hydroxy group in one molecule may be used.

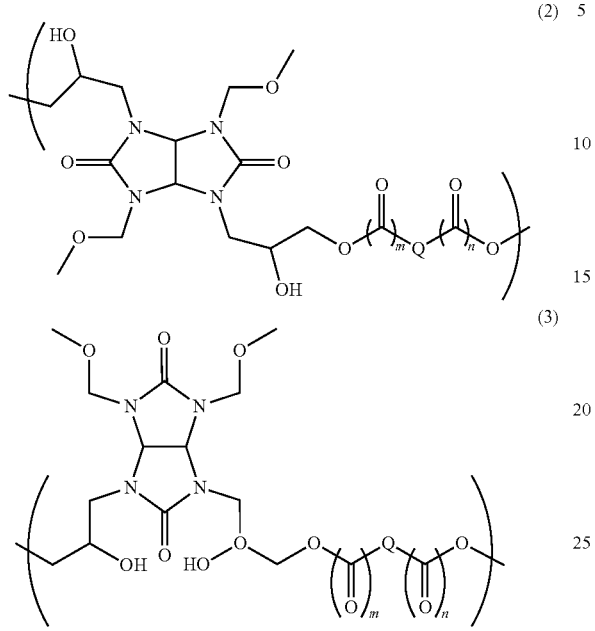

(wherein Q is a divalent organic group having a carbon atom number of 1 to 16 and optionally having at least one hetero atom; and m and n are each independently 0 or 1).

EXAMPLES

The present invention will be described hereinafter with reference to synthesis examples and examples, although the present invention is not particularly limited thereto.

The purity shown herein in the following synthesis examples was measured by high performance liquid chromatography (hereinafter abbreviated as HPLC). The measurement was performed using a HPLC apparatus (L-2000 series) from Hitachi High-Technologies Corporation. The measurement conditions and the like were as follows:

HPLC column: Inertsil [registered trademark] ODS-3 (GL Sciences Inc.)
Column temperature: 40° C.
Solvent: acetonitrile/10 mM aqueous solution of ammonium formate=3/7 (v/v) (0-10 min), the composition ratio was changed from 3/7 (v/v) to 7/3 (v/v) (10-15 min), 7/3 (v/v) (15-25 min), the composition ratio was changed from 7/3 (v/v) to 3/7 (v/v) (25-30 min), 3/7 (v/v) (30-35 min)
Flow rate: 1.0 mL/min The weight average molecular weights shown herein in the following synthesis examples were measured by gel permeation chromatography (hereinafter abbreviated as GPC). The measurement was performed using a GPC apparatus (HLC-8320GPC) from Tosoh Corporation. The measurement conditions and the like were as follows:

GPC column: KF-403HQ, KF-402HQ, and KF-401HQ (from Showa Denko K.K.)
Column temperature: 40° C.
Solvent: tetrahydrofuran (THF)
Flow rate: 0.5 mL/min
Standard sample: polystyrene (from Showa Denko K.K.)

Synthesis Example 1

Synthesis of 1,4-diallylglycoluril

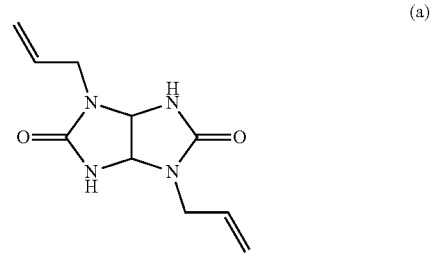 [SMILES: C=CCN1C(=O)NC2C1NC(=O)N2CC=C]

In a 1 L flask equipped with a condenser, a thermometer, and a stirrer, 200.00 g (2.00 mol) of allylurea (from Tokyo Chemical Industry Co., Ltd.), 400.00 g (2.00 parts) of pure water, 110.37 g (0.74 mol) of a 39% by mass aqueous solution of glyoxal (from Tokyo Chemical Industry Co., Ltd.), and 24.0 g (0.12 parts) of concentrated hydrochloric acid (from Kanto Chemical Co., Inc., special grade) were placed, and the contents were heated to 90° C. and stirred for 3 hours. Then, the reaction solution in the flask was cooled to 5° C., the precipitated crystals were filtered, and the filtered product was washed twice with 100 g of cold water. The resulting residue was dried under reduced pressure to obtain 50.53 g of 1,4-diallylglycoluril of formula (a) as a white solid. The yield of the resulting compound was 29.89%, and the purity of the resulting compound as measured by HPLC was 100%.

The δ value in the $^1$H-NMR spectrum (DMSO-d6) of the resulting 1,4-diallylglycoluril was as follows:
7.63 (s, 2H), 5.73 (m, 2H), 5.19 (dd, 4H), 5.18 (s, 2H), 3.90 (dd, 2H), 3.49 (dd, 2H)

Synthesis Example 2

Synthesis of 1,4-diallyl-3,6-dimethylolglycoluril

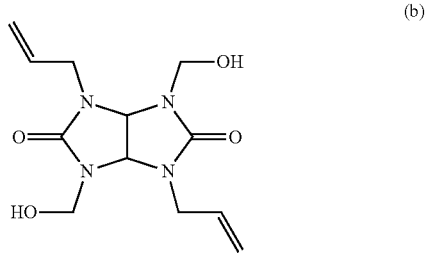 [SMILES: C=CCN1C(=O)N(CO)C2C1N(CO)C(=O)N2CC=C]

In a 500 mL flask equipped with a condenser, a thermometer, and a stirrer, 45.65 g (0.56 mol) of a 37% by mass aqueous solution of formaldehyde (from Tokyo Chemical Industry Co., Ltd.), 1.94 g (0.04 part) of a 0.5 N aqueous solution of sodium hydroxide, and 250.00 g (5.00 parts) of pure water were placed, and the contents were heated to 40° C. and stirred. At the same temperature, 50.00 g (0.23 mol) of 1,4-diallylglycoluril obtained in Synthesis Example 1 above was added, and then the contents were heated to 55° C. and stirred for 1.5 hours. Then, the reaction solution in the flask was cooled to 25° C., and 0.44 g of a 0.5 N aqueous solution of sodium hydroxide was added thereto. Furthermore, the reaction solution was cooled to 20° C., the precipitated crystals were filtered, and the filtered product was washed twice with 50.00 g (1.00 part) of ethyl acetate. The resulting residue was dried under reduced pressure to obtain 48.50 g of 1,4-diallyl-3,6-dimethylolglycoluril of formula (b) as a white solid. The yield of the resulting compound was 76.37%, and the purity of the resulting compound as measured by HPLC was 100%.

The δ value in the $^1$H-NMR spectrum (DMSO-d6) of the resulting 1,4-diallyl-3,6-dimethylolglycoluril was as follows:

5.93 (t, 2H), 5.76 (m, 2H), 5.37 (s, 2H), 5.17 (dd, 4H), 4.63 (m, 4H), 4.02 (dd, 2H), 3.86 (dd, 2H)

Synthesis Example 3

Synthesis of
1,4-diallyl-3,6-di(methoxymethyl)glycoluril

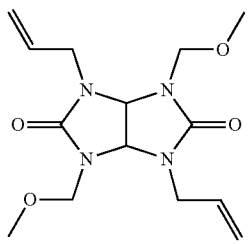

(c)

In a 300 mL flask equipped with a condenser, a thermometer, and a stirrer, 48.00 g (0.17 mol) of 1,4-diallyl-3,6-dimethylolglycoluril obtained in Synthesis Example 2 above, 109.0 g of methanol, and 3.67 g (0.04 mol) of 65% by mass nitric acid were placed, and the contents were heated to 40° C. and stirred for 2 hours. Then, the reaction solution in the flask was cooled to 25° C., 8.14 g of a 20% by mass aqueous solution of sodium hydroxide was added thereto, and the solvent was distilled off at 40° C. under reduced pressure. To the resulting concentrate, 480.30 g (10.00 parts) of toluene and 240.00 g (5.00 parts) of pure water were added, and the phases were separated. To the organic phase, 240.00 g (5.00 parts) of pure water was further added, and the phases were separated; thereafter, the solvent in the resulting organic phase was distilled off at 40° C. under reduced pressure to obtain 41.10 g of 1,4-diallyl-3,6-di(methoxymethyl)glycoluril of formula (c) as a white solid. The yield of the resulting compound was 77.9%, and the purity of the resulting compound as measured by HPLC was 99.49%.

The δ value in the $^1$H-NMR spectrum (DMSO-d6) of the resulting 1,4-diallyl-3,6-di(methoxymethyl)glycoluril was as follows:

5.74 (m, 2H), 5.35 (s, 2H), 5.19 (m, 4H), 4.61 (dd, 4H), 4.09 (dd, 2H), 3.76 (dd, 2H), 3.17 (s, 6H)

Synthesis Example 4

Synthesis of
1,4-diglycidyl-3,6-di(methoxymethyl)glycoluril

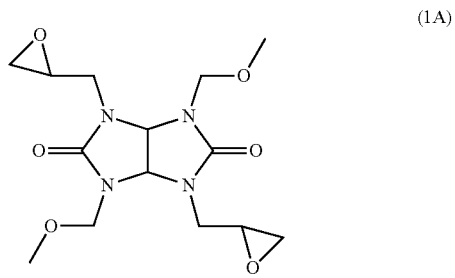 [SMILES: COCN1C(=O)N(CC2CO2)C2C1N(CC1CO1)C(=O)N2COC]

(1A)

In a 1 L flask equipped with a condenser, a thermometer, and a stirrer, 40.00 g (0.13 mol) of 1,4-diallyl-3,6-di(methoxymethyl)glycoluril obtained in Synthesis Example 3 above and 400.00 g (10.00 parts) of chloroform were placed, and the contents were cooled to 0° C. and stirred. At the same temperature, 82.12 g (0.31 mol) of 65% by mass m-chloroperoxybenzoic acid (from Tokyo Chemical Industry Co., Ltd.) was added, and then the contents were heated to 25° C. and stirred for 38.5 hours. Then, 400.00 g (10.00 parts) of chloroform was added to the reaction solution in the flask, 800.00 g (20.00 parts) of a 5% by mass aqueous solution of sodium hydrogen carbonate was further added dropwise, and the phases were separated. Next, 800.00 g (20.00 parts) of a 10% by mass aqueous solution of sodium sulfite was added to the organic phase, and the phases were separated. To the organic phase, 800.00 g (20.00 parts) of a 5% by mass aqueous solution of sodium hydrogen carbonate was further added, and the phases were separated. Lastly, 800.00 g (20.00 parts) of pure water was added to the organic phase, and the phases were separated. The solvent in the resulting organic phase was distilled off at 30° C. under reduced pressure. To the resulting residue, 160.00 g (4.00 parts) of cyclopentyl methyl ether was added, the precipitated crystals were filtered, and the filtered product was washed twice with 20.00 g (0.50 parts) of cyclopentyl methyl ether. The resulting residue was dried at 30° C. under reduced pressure to obtain 21.54 g of 1,4-diglycidyl-3,6-di(methoxymethyl)glycoluril of formula (1A) as a white solid. The yield of the resulting compound was 48.82%, and the purity of the resulting compound as measured by HPLC was 96.70%.

[Method of Pre-Treatment for an Anion Exchange Resin and a Cation Exchange Resin]

Propylene glycol monomethyl ether (2.0 kg) was added to an anion exchange resin (2.0 kg), and the mixture was stirred for 4 hours and then filtered. To the anion exchange resin, propylene glycol monomethyl ether (2.0 kg) was added again, and the mixture was stirred for 8 hours and then filtered. To the anion exchange resin, propylene glycol monomethyl ether (2.0 kg) was further added, and the mixture was stirred for 4 hours and then stored. The stored anion exchange resin to which propylene glycol monomethyl ether was added was filtered immediately before being used in the following synthesis examples.

Propylene glycol monomethyl ether (4.0 kg) was added to a cation exchange resin (2.0 kg), and the mixture was stirred for 4 hours and then filtered. To the cation exchange resin, propylene glycol monomethyl ether (2.0 kg) was added again, and the mixture was stirred for 8 hours and then filtered. To the cation exchange resin, propylene glycol monomethyl ether (2.0 kg) was further added, and the mixture was stirred for 4 hours and then stored. The stored cation exchange resin to which propylene glycol monomethyl ether was added was filtered immediately before being used in the following synthesis examples.

Synthesis Example 5

2.01 g of 1,4-diglycidyl-3,6-di(methoxymethyl)glycoluril obtained in Synthesis Example 4 above, 1.29 g of 3,3'-dithiodipropionic acid (Sakai Chemical Industry Co., Ltd., trade name: DTDPA), and 0.11 g of triphenylmonoethylphosphonium bromide that is a quaternary phosphonium salt as a catalyst were dissolved in 13.60 g of propylene glycol monomethyl ether, and then the solution was heated to 105° C. and stirred in a nitrogen atmosphere for 24.5 hours. To the resulting reaction product, 2.86 g of the anion exchange resin (product name: DOWEX [registered trademark] MONOSPHERE [registered trademark] 550A; Muromachi Technos Co., Ltd.) pre-treated above and 2.86 g of the cation exchange resin (product name: AMBERLYST [registered trademark] 15JWET; Organo Corporation) pre-treated above were added, and the mixture was stirred at 25 to 30° C. for 4 hours and then filtered. GPC analysis of the varnish solution after the ion exchange treatment showed that the weight average molecular weight relative to standard polystyrene was 6,630. This reaction product has a repeating unit structure of formula (2A):

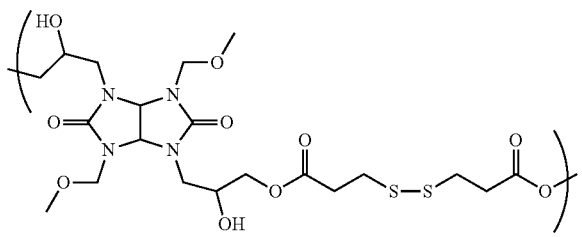

(2A)

Synthesis Example 6

2.0 g of monoallyl diglycidyl isocyanurate (Shikoku Chemicals Corporation, trade name: MADGIC), 1.56 g of 3,3'-dithiodipropionic acid (Sakai Chemical Industry Co., Ltd., trade name: DTDPA), and 0.13 g of triphenylmonoethylphosphonium bromide that is a quaternary phosphonium salt as a catalyst were dissolved in 14.82 g of propylene glycol monomethyl ether, and then the solution was heated to 105° C. and stirred in a nitrogen atmosphere for 24.5 hours. To the resulting reaction product, 3.22 g of the anion exchange resin used in Synthesis Example 5 above and 3.22 g of the cation exchange resin used in Synthesis Example 5 above were added, and the mixture was stirred at 25 to 30° C. for 4 hours and then filtered. GPC analysis of the varnish solution after the ion exchange treatment showed that the weight average molecular weight relative to standard polystyrene was 6,165. This reaction product has a repeating unit structure of formula (4):

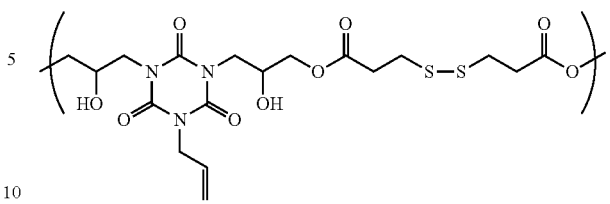

(4)

Example 1

To 1.838 g of the solution containing 0.364 g of the reaction product obtained in Synthesis Example 5 above, 8.158 g of propylene glycol monomethyl ether, 0.013 g of pyridinium p-toluenesulfonate, and 0.004 g of a surfactant (DIC Corporation, trade name: R-40-LM) were added to form a solution. The solution was filtered through a polyethylene microfilter having a pore size of 0.45 μm to prepare a film-forming composition.

Comparative Example 1

To 1.898 g of the solution containing 0.364 g of the reaction product obtained in Synthesis Example 6 above, 8.087 g of propylene glycol monomethyl ether, 0.013 g of pyridinium p-toluenesulfonate, and 0.004 g of a surfactant (DIC Corporation, trade name: R-40-LM) were added to form a solution. The solution was filtered through a polyethylene microfilter having a pore size of 0.45 μm to prepare a film-forming composition.

Comparative Example 2

To 1.475 g of the solution containing 0.283 g of the reaction product obtained in Synthesis Example 6 above, 8.424 g of propylene glycol monomethyl ether, 0.010 g of pyridinium p-toluenesulfonate, 0.085 g of tetramethoxymethylglycoluril (Nihon Cytec Industries Inc., trade name: POWDERLINK [registered trademark] 1174) as a crosslinking agent, and 0.003 g of a surfactant (DIC Corporation, trade name: R-40-LM) were added to form a solution. The solution was filtered through a polyethylene microfilter having a pore size of 0.45 μm to prepare a film-forming composition.

(Stripping Test)

Each of the film-forming compositions prepared in Example 1, and Comparative Examples 1 and 2 described herein was applied by a spin coater onto a silicon wafer. This silicon wafer was placed on a hot plate, and baked at 215° C. for 1 minute to form a thin film on the silicon wafer (film thickness: about 100 nm). The thin film formed was subsequently immersed in a solvent (propylene glycol monomethyl ether/propylene glycol monomethyl ether acetate=7/3) for 1 minute (stripping), and then the solvent was removed by a spinner. The thin film was baked on a hot plate at 100° C. for 30 seconds to be dried, and then the film thickness of the thin film was measured. The results shown in Table 1 below were obtained.

As is clear from the results shown in Table 1, a cured film having solvent resistance was obtained using the film-forming composition of Example 1, which contained the reaction product obtained in Synthesis Example 5 above, and did not contain a crosslinking agent. In contrast, a cured film having solvent resistance was not obtained using the film-forming composition of Comparative Example 1, which contained the reaction product obtained in Synthesis Example 6 above, and did not contain a crosslinking agent. This result shows that the reaction product obtained in Synthesis Example 5 used in Example 1 has a self-crosslinking ability.

TABLE 1

| | Crosslinking Agent | Film Thickness [nm] | | Remaining Film Ratio [%] |
| --- | --- | --- | --- | --- |
| | | Before Stripping | After Stripping | |
| Example 1 | No | 99.9 | 96.8 | 96.9 |
| Comparative Example 1 | No | 100.6 | 6.0 | 5.9 |
| Comparative Example 2 | Yes | 100.5 | 99.9 | 99.5 |

INDUSTRIAL APPLICABILITY

The nitrogen-containing cyclic compounds produced in accordance with the present invention can be applied to, for example, anti-reflective coating-forming compositions for lithography, resist underlayer film-forming compositions, resist upper layer film-forming compositions, photocurable resin compositions, thermosetting resin compositions, planarization film-forming compositions, adhesive compositions, or other compositions.

The invention claimed is:

1. A nitrogen-containing cyclic compound of formula (1):

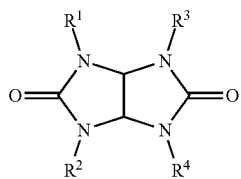

(1)

wherein any two of $R^1$, $R^2$, $R^3$, and $R^4$ are glycidyl groups, and the remaining two are methoxymethyl groups.

2. The nitrogen-containing cyclic compound according to claim 1, wherein the nitrogen-containing cyclic compound of formula (1) is represented by formula (1A) or (1B):

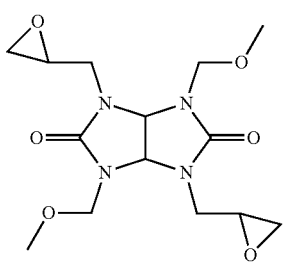

(1A)

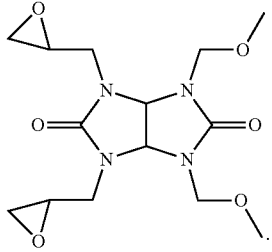

(1B)

3. A method for producing the nitrogen-containing cyclic compound according to claim 2, comprising:

a first step of obtaining a compound of formula (b) by reacting a compound of formula (a) with formaldehyde in a basic aqueous solution;

a second step of obtaining a compound of formula (c) by reacting the compound of formula (b) with methanol in an acid solution of the methanol; and a third step of obtaining the nitrogen-containing cyclic compound of formula (1A) by reacting the compound of formula (c) with an oxidizing agent in an organic solvent:

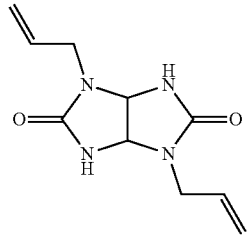

(a)

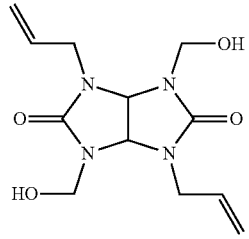

(b)

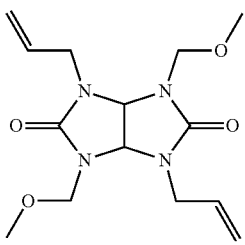

(c)

4. A method for producing the nitrogen-containing cyclic compound according to claim 2, comprising:

a first step of obtaining a compound of formula (e) by reacting a compound of formula (d) with formaldehyde in a basic aqueous solution;

a second step of obtaining a compound of formula (f) by reacting the compound of formula (e) with methanol in an acid solution of the methanol; and
a third step of obtaining the nitrogen-containing cyclic compound of formula (1B) by reacting the compound of formula (f) with an oxidizing agent in an organic solvent:
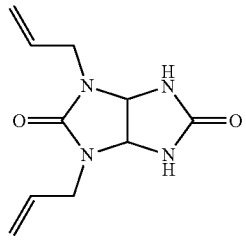
(d)
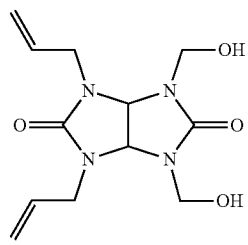
(e)
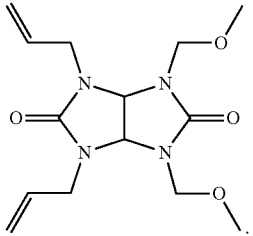
(f)
* * * * *